United States Patent
Sugiyama et al.

(10) Patent No.: US 8,268,625 B2
(45) Date of Patent: Sep. 18, 2012

(54) METHOD OF MEASURING GLYCATED HEMOGLOBIN CONCENTRATION AND CONCENTRATION MEASURING APPARATUS

(75) Inventors: Koji Sugiyama, Kyoto (JP); Toshikatsu Sakai, Kyoto (JP)

(73) Assignee: Arkray, Inc., Kyoto (JP)

( * ) Notice: Subject to any disclaimer, the term of this patent is extended or adjusted under 35 U.S.C. 154(b) by 360 days.

(21) Appl. No.: 12/225,540

(22) PCT Filed: Mar. 23, 2007

(86) PCT No.: PCT/JP2007/056110
§ 371 (c)(1),
(2), (4) Date: Jul. 26, 2010

(87) PCT Pub. No.: WO2007/111282
PCT Pub. Date: Oct. 4, 2007

(65) Prior Publication Data
US 2010/0291691 A1    Nov. 18, 2010

(30) Foreign Application Priority Data

Mar. 24, 2006  (JP) .................................. 2006-082095

(51) Int. Cl.
*G01N 33/72* (2006.01)
*G01N 21/25* (2006.01)

(52) U.S. Cl. .............. 436/67; 436/63; 436/66; 436/161; 436/164; 422/70; 422/82.05; 422/82.09; 356/432; 356/436

(58) Field of Classification Search .................... 436/63, 436/66, 67, 161, 164, 171; 422/70, 82.05, 422/82.09; 356/319, 320, 432, 433, 436
See application file for complete search history.

(56) References Cited

U.S. PATENT DOCUMENTS

| | | | |
|---|---|---|---|
| 4,407,961 A * | 10/1983 | Sanders | 436/67 |
| 4,465,774 A * | 8/1984 | Huang et al. | 436/15 |
| 5,294,336 A | 3/1994 | Mizuno | |
| 5,541,117 A | 7/1996 | Karl et al. | |
| 5,543,315 A * | 8/1996 | Sugiyama et al. | 436/161 |
| 5,644,503 A | 7/1997 | Ito et al. | |
| 5,692,503 A | 12/1997 | Kuenstner | |

(Continued)

FOREIGN PATENT DOCUMENTS
EP    0 072 440 A1    7/1982

(Continued)

OTHER PUBLICATIONS

A. Zwart et al., Multicomponent Analysis of Hemoglobin derivatives with a Reversed-Optics Spectrophotometer, vol. 30, No. 3, pp. 373-379, Clinical Chemistry, (1984).

(Continued)

*Primary Examiner* — Maureen Wallenhorst
(74) *Attorney, Agent, or Firm* — Rader, Fishman & Grauer PLLC

(57) ABSTRACT

When the concentration of glycated hemoglobin is measured, a plurality of wavelengths are selected as measurement wavelengths from the wavelength range of 400 to 450 nm. Preferably, by use of a liquid chromatography, at least the light of different peak wavelengths in the wavelength range of 415 to 430 nm are continuously or intermittently received to obtain a three dimensional chromatogram having as variables the wavelength, the elution time and the amount of detection. The concentration of glycated hemoglobin is calculated based on this three dimensional chromatogram.

10 Claims, 13 Drawing Sheets

U.S. PATENT DOCUMENTS

| | | |
|---|---|---|
| 2002/0137993 A1 | 9/2002 | Pickard |
| 2003/0009090 A1 | 1/2003 | Jeon et al. |

FOREIGN PATENT DOCUMENTS

| | | | |
|---|---|---|---|
| EP | 0 294 121 A2 | | 5/1988 |
| EP | 0 631 137 A2 | | 5/1994 |
| JP | 05-113441 A | | 5/1993 |
| JP | 05-256851 A | | 10/1993 |
| JP | 06-011510 A | | 1/1994 |
| JP | 06-308120 A | | 11/1994 |
| JP | 07-120447 A | | 5/1995 |
| JP | 07-270387 A | | 10/1995 |
| JP | 08-159954 A | | 6/1996 |
| JP | 08-233824 A | | 9/1996 |
| JP | 11-142326 | * | 5/1999 |
| JP | 2002-369814 A | | 12/2002 |
| JP | 2004-526141 A | | 8/2004 |
| JP | 2004-309250 A | | 11/2004 |
| WO | WO-2004/057285 A1 | | 7/2004 |

OTHER PUBLICATIONS

PCT International Search Report (2 sheets), May 29, 2007.
European Search Report Communication 8 sheets and Supplementary European Search Report dated May 27, 2009 3 sheets.

* cited by examiner

METHOD OF MEASURING GLYCATED HEMOGLOBIN CONCENTRATION AND CONCENTRATION MEASURING APPARATUS

TECHNICAL FIELD

The present invention relates to a technique that measures the concentration of glycated hemoglobin contained in a sample of blood or the like.

BACKGROUND ART

When biological components are separated and analyzed by use of biological samples of blood or the like, high-performance liquid chromatography apparatus (HPLC apparatus) using high performance liquid chromatography (HPLC) are widely used (e.g., refer to Patent Document 1).

As shown in FIG. 13, a general HPLC apparatus 9 is configured to prepare a sample containing biological components in a sample preparation unit 90 and then to introduce the sample into an analytical column 91 to thereby adsorb the biological components to a filler of the analytical column 91. When glycated hemoglobin is measured by using whole blood as a sample, red blood cells collected from whole blood are hemolyzed and then a biological sample in a state in which the laked blood is diluted is introduced into the analytical column 91. On the other hand, a biological component adsorbed on a filler is eluted by supplying an eluent from an eluent bottle 93 to the analytical column 91 by a liquid feed pump 92. The eluent including the biological component from the analytical column 91 is introduced into a photometry mechanism 94, where the biological component is analyzed by continuously measuring the absorbance of the eluent including the biological component.

As shown in FIG. 14, the photometry mechanism 94 radiates light from a light source 97 while the eluent including the biological component flows through a path 96 of a photometry cell 95 and receives a transmitted beam at that time in a light receiving section 98. The wavelength of light received in a light receiving section 98 is selected in an interference filter 99, while a signal of an output level corresponding to the amount of light received is output from the light receiving section 98. Since the photometry of an eluent in the photometry mechanism 94 is continuously executed, the relationship between the elution time and the amount of light received (absorbance) is obtained as a chromatogram shown in FIG. 15.

The HPLC apparatus 9 further calculates the total amount of hemoglobin based on a chromatogram that is a change with the lapse of time of absorbance and also calculates the glycated hemoglobin concentration as a proportion occupied by the amount of glycated hemoglobin in the total amount of hemoglobin (part shown by a cross hatching in FIG. 15).

However, the amount of dissolution in an eluent of a gas such as oxygen varies depending on the temperature of the eluent. Therefore, when the temperature (environmental temperature) outside the apparatus varies or the biological component is analyzed in a state at a different environmental temperature, the state of a dissolved gas in an eluent (amount of dissolution) is different. Hence, when the dissolved oxygen concentration in an eluent varies along with the variation of environmental temperature, or the like, the ratio of the amounts of oxyhemoglobin and deoxyhemoglobin in hemoglobin varies. In addition, even in a biological sample introduced into the analytical column 91, the ratio of the amounts of oxyhemoglobin and deoxyhemoglobin in hemoglobin can vary at each measurement of each time.

On the other hand, a sample is used that has a relatively large amount of oxygen by dilution of laked blood, as a biological sample introduced into the analytical column 91, and therefore 415 nm that is the maximum absorption wavelength of oxyhemoglobin is adopted as a measurement wavelength in the photometry mechanism 94. Thus, under environments in which the change in environmental temperature is large, or the like, the ratios of the amounts of oxyhemoglobin and deoxyhemoglobin vary, whereby precise measurements become difficult when they are measured at the same wavelength.

Patent Document 1: Japanese Patent Laid-Open No. 7-120447

DISCLOSURE OF THE INVENTION

Problems to be Solved by the Invention

An object of the present invention is to be able to appropriately measure the concentration of glycated hemoglobin even when the ratio of amounts of oxyhemoglobin and deoxyhemoglobin is different.

Means for Solving the Problem

A method of measuring glycated hemoglobin concentration provided in a first aspect of the present invention is a method of measuring the concentration of glycated hemoglobin based on light that travels from a sample when the sample is irradiated with light, characterized in that the concentration of the glycated hemoglobin is measured based on light of a plurality of measurement wavelengths having a peak wavelength in the wavelength range of 400 to 450 nm.

Preferably, light of different peak wavelengths in the wavelength range of at least 415 to 430 nm among the light that travels from a sample is continuously or intermittently received to thereby measure the concentration of glycated hemoglobin.

The present invention can be applied to a method of measuring the concentration of glycated hemoglobin making use of liquid chromatography. In that case, the concentration of glycated hemoglobin is calculated, for example, based on a three dimensional chromatogram in which the measurement wavelength, the elution time and the amount of detection are made variables. More specifically, for instance, the concentration of glycated hemoglobin is calculated as a proportion occupied by the volume or integrated value corresponding to the glycated hemoglobin in the volume or integrated value corresponding to the total amount of hemoglobin in the above three dimensional chromatogram. The concentration of glycated hemoglobin may be obtained by calculation of the proportion of the glycated hemoglobin from a chromatogram in which the elution time and the amount of detection in each measurement wavelength are made variables and also by averaging of the proportion of the glycated hemoglobin in each measurement wavelength.

The concentration of glycated hemoglobin can also be calculated as a proportion occupied by an area corresponding to glycated hemoglobin in an area corresponding to the total amount of hemoglobin in a two dimensional chromatogram with the peak value and elution time of the detection value of hemoglobin in each measurement wavelength.

The concentration of glycated hemoglobin can be also measured based on a first quantity of light that is an amount of light having a peak wavelength in the wavelength range of 400 to 420 nm, traveling from a sample, and a second quantity of light that is an amount of light having a peak wavelength in the wavelength range of 420 to 440 nm, traveling from the sample. In this case, the concentration of oxyhemoglobin or a value that correlates to this concentration based on the above-mentioned first quantity of light is calculated, while the concentration of deoxyhemoglobin or a value that correlates to this concentration based on the above-mentioned second quantity of light is calculated. Then, the oxyhemoglobin and deoxyhemoglobin concentrations are added up, or a value that correlates to the oxyhemoglobin concentration and a value that correlates to the deoxyhemoglobin concentration are added up to thereby be able to calculate the concentration of the glycated hemoglobin.

When the glycated hemoglobin concentration method of the present invention utilizes liquid chromatography, the concentration of glycated hemoglobin may be calculated based on a chromatogram produced by overlapping a first chromatogram that corresponds to the oxyhemoglobin indicating the relationship between the elution time and the amount of detection obtained based on the above first quantity of light and a second chromatogram that corresponds to the deoxyhemoglobin indicating the relationship between the elution time and the amount of detection obtained based on the second quantity of light.

The above-mentioned sample is obtained, for example, by hemolyzing a blood cell.

In a second aspect of the present invention, provided is an apparatus of measuring the concentration of glycated hemoglobin including a photometry mechanism in which a sample is irradiated with light from a light source and at the time a light receiving section receives light that travels from the sample, characterized in that the above photometry mechanism is configured to distinguish light of a plurality of wavelengths having a peak wavelength in the wavelength range of 400 to 450 nm and be capable of receiving light in the light receiving section.

Preferably, the light receiving section is configured to be continuously or intermittently able to receive light of different peak wavelengths in the wavelength range of at least 415 to 430 nm.

The present invention can be applied to an apparatus of measuring the concentration of glycated hemoglobin making use of liquid chromatography. The apparatus of measuring the concentration of glycated hemoglobin further includes a calculating section configured to calculate the glycated hemoglobin concentration based on a three dimensional chromatogram in which the wavelength, the elution time and the amount of detection are made variables.

The calculating section is configured to calculate, for example, the concentration of glycated hemoglobin as a proportion occupied by the volume or integrated value corresponding to the glycated hemoglobin in the volume or integrated value corresponding to the total amount of hemoglobin in the above three dimensional chromatogram. More specifically, the calculating section is configured to calculate the concentration of glycated hemoglobin as a proportion occupied by an area corresponding to the glycated hemoglobin in an area corresponding to the total amount of hemoglobin, for example, in a two dimensional chromatogram in which the elution time and the peak value of the amount of detection obtained based on the above three dimensional chromatogram are made variables. The calculating section may be also configured to calculate the proportion of glycated hemoglobin from a chromatogram in which the elution time and the amount of detection in each peak wavelength are made variables and also to calculate the glycated hemoglobin concentration by averaging the proportion of the glycated hemoglobin in each peak wavelength. The calculating section can be also configured to calculated as a proportion occupied by an area corresponding to glycated hemoglobin in an area corresponding to the total amount of hemoglobin in a two dimensional chromatogram with the peak value and elution time of the detection value of hemoglobin in each peak wavelength.

The apparatus of measuring the concentration of glycated hemoglobin of the present invention can also include a calculating section of calculating the glycated hemoglobin concentration based on a first quantity of light that is an amount of light having a peak wavelength in the wavelength range of 400 to 420 nm, traveling from a sample, and a second quantity of light that is an amount of light having a peak wavelength in the wavelength range of 420 to 440 nm, traveling from the sample. The calculating section is configured to calculate, for example, the concentration of oxyhemoglobin or a value that correlates to this concentration based on the above-mentioned first quantity of light on the one hand, and to calculate the concentration of deoxyhemoglobin or a value that correlates to this concentration based on the above-mentioned second quantity of light on the other, and also to add up the above oxyhemoglobin concentration and the above deoxyhemoglobin concentration or to add up a value that correlates to the above oxyhemoglobin concentration and a value that correlates to the above deoxyhemoglobin concentration to thereby calculate the concentration of the glycated hemoglobin.

When the glycated hemoglobin concentration apparatus of the present invention utilizes liquid chromatography, the calculating section may also be configured to calculate the concentration of glycated hemoglobin based on a chromatogram produced by overlapping a first chromatogram that corresponds to the oxyhemoglobin indicating the relationship between the elution time and the amount of detection obtained based on the above first quantity of light and a second chromatogram that corresponds to the deoxyhemoglobin indicating the relationship between the elution time and the amount of detection obtained based on the above second quantity of light.

The above-mentioned sample is obtained, for example, by hemolyzing a blood cell.

EXPLANATION OF SYMBOLS

X: HPLC apparatus (glycated hemoglobin determination apparatus)
5: Photometry mechanism
51: Light source (of photometry mechanism)
53B: Light receiving element (light receiving section) (of photometry mechanism)
61: Calculating section

BEST MODE FOR CARRYING OUT THE INVENTION

Hereinafter, first to third embodiments of the present invention will be specifically described with reference to the drawings.

First, the first embodiment of the present invention will be described with reference to FIGS. 1 to 6.

Figure 1:
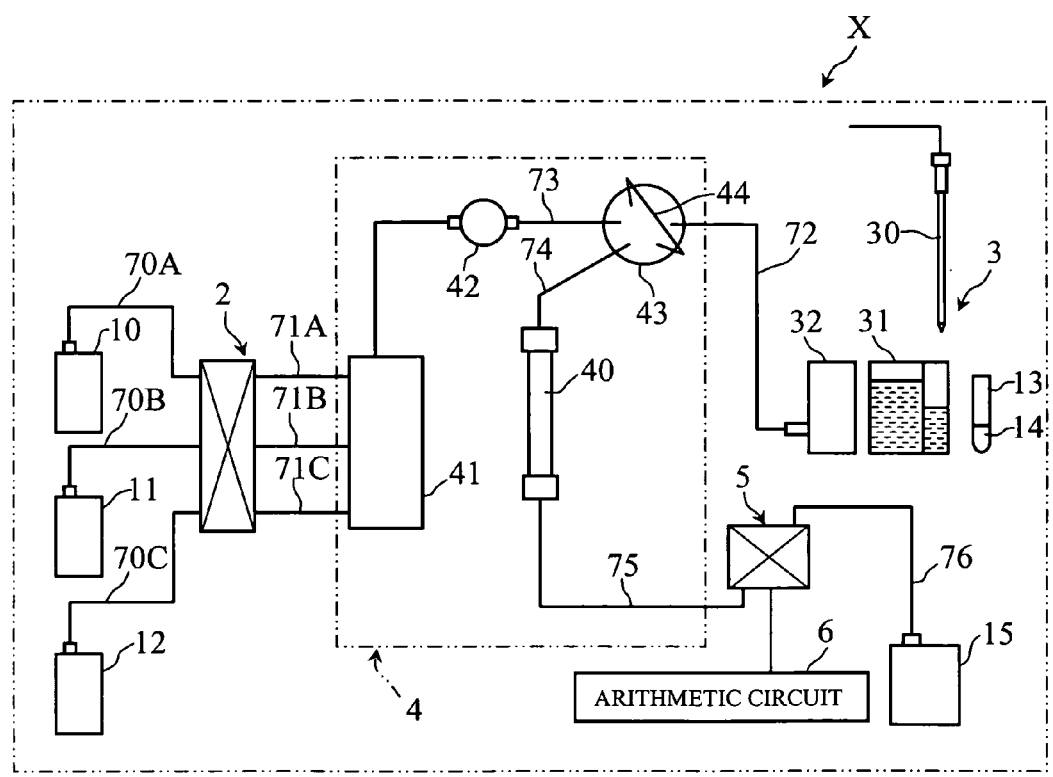
FIG. 1 is a schematic block diagram showing an HPLC apparatus that is one example of a glycated hemoglobin measuring apparatus according to a first embodiment of the present invention.

HPLC apparatus X shown in FIG. 1 corresponds to one example of the glycated hemoglobin concentration measuring apparatus of the present invention. This apparatus is configured to measure the concentration of glycated hemoglobin by use of whole blood. This HPLC apparatus X includes a plurality of eluent bottles 10, 11, and 12 (three bottles in the figure), a deaerator 2, a sample preparation unit 3, an analysis unit 4, a photometry mechanism 5, and an arithmetic circuits 6.

Each of the eluent bottles 10, 11, 12 keeps an eluent that is to be supplied to an analytical column 40 described below. Eluents make use of buffers different in, for example, pH or salt concentration.

The deaerator 2 removes a dissolved gas from an eluent prior to supplying the eluent to the analysis unit 4 (analytical column 40) and is connected to the eluent bottles 10, 11, 12 through lay pipes 70A, 70B, 70C and to a manifold 41 of the analysis unit 4 via lay pipes 71A, 71B, 71C.

As shown in FIG. 1, the sample preparation unit 3 prepares a sample that is introduced into the analytical column 40 from blood cell components collected from a blood collection tube 13. This sample preparation unit 3 has a sampling nozzle 30, a preparation tank 31 and a dilution bath 32.

The sampling nozzle 30 collects a variety of liquids including a blood sample 14 of the blood collection tube 13, is capable of the aspiration and the discharge of a liquid and also is movable vertically and horizontally. The operation of this sampling nozzle 30 is controlled by a control unit (not illustrated).

The preparation tank 31 keeps a preparation for preparing a sample for introduction introduced into the analytical column 40 based on the blood sample 14. This preparation tank 31 keeps as a preparation laked blood for hemolyzing a red blood cell, a diluting fluid for diluting laked blood, or the like.

The dilution bath 32 provides a place for hemolyzing a red blood cell in the blood sample 14 and dilute laked blood to prepare a sample for introduction. This dilution bath 32 is connected to an injection valve 43 in the analysis unit 4 described below through piping 72 and configured to be able to introduce a sample for introduction prepared in the dilution bath 32 into the analytical column 40 through the injection valve 43.

The analysis unit 4 controls the adsorption and elution of a biological component to the filler of the analytical column 40 and supplies various biological components to the photometry mechanism 5, and is temperature controlled by a temperature control mechanism (not illustrated). The temperature in the analysis unit 4 is set, for example, at about 40° C. The analytical column 40 keeps a filler for selectively adsorb hemoglobin in a sample. A methacrylate copolymer is used, for example, as a filler.

The analysis unit 4 has a manifold 41, the liquid feed pump 42, and the injection valve 43 in addition to the analytical column 40.

The manifold 41 selectively supplies an eluent from specific eluent bottles 10, 11, 12 of a plurality of eluent bottles 10, 11, 12, to the injection valve 43. This manifold 41 is connected to the deaerator 2 through the lay pipes 71A, 71B, 71C, and connected to the injection valve 43 through piping 73.

The liquid feed pump 42 imparts a power to move an eluent to the analytical column 40 through the injection valve 43 and is provided on the way of piping 73. The liquid feed pump 42 is operated so that the flow rate of an eluent may become, for example, from 1.0 to 2.0 ml/min.

The injection valve 43 can collect the sample for introduction of a given quantity and introduce the sample for introduction into the analytical column 40, and includes a plurality of introduction ports and exhaust ports (their illustrations are omitted). An injection loop 44 is connected to this injection valve 43. This injection loop 44 can keep a liquid of a given quantity (e.g., several μL), and can select a state in which the injection valve 43 is accordingly switched to thereby communicate the injection loop 44 with the dilution bath 32 and supply a sample for introduction from the dilution bath 32 to the injection loop 44, a state in which the injection loop 44 is communicated with the analytical column 40 via piping 74 to introduce a sample for introduction from the injection loop 44 to the analytical column 40, or a state in which a cleaning solution is supplied to the injection loop 44 from a cleaning tank (not illustrated). As such an injection valve 43, for example, a hexagonal valve can be used.

Figure 2:
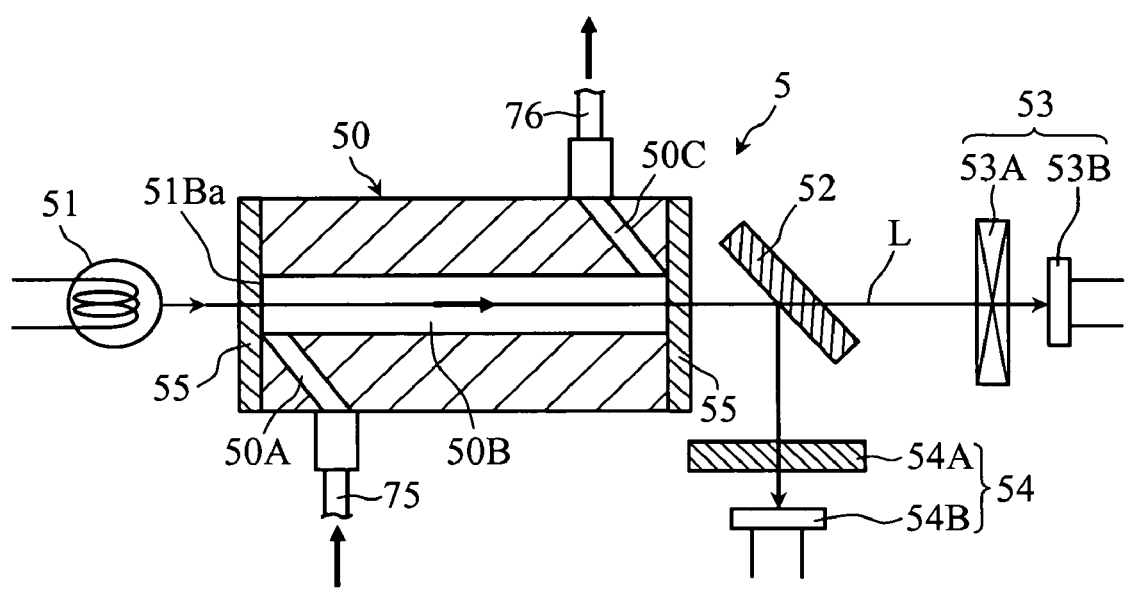
FIG. 2 is a cross-sectional view for describing a photometry mechanism in the HPLC apparatus shown in FIG. 1.

As shown in FIG. 2, the photometry mechanism 5 optically detects hemoglobin contained in an eluent from the analytical column 40 and has a photometry cell 50, a light source 51, a beam splitter 52, a light receiving system 53 for measurement and a receiving system 54 for reference.

The photometry cell 50 defines the photometry area. This photometry cell 50 has an introduction path 50A and a photometry path 50B and a discharge path 50C, and these paths 50A, 50B, 50C are communicated in series. The introduction path 50A introduces an eluent from the analytical column 40 (see FIG. 1) into the photometry path 50B, and is connected to the analytical column 40 through piping 75. The photometry path 50B provides a place for flowing of an eluent to be a photometry target and for photometry of an eluent and is formed in a linear fashion. This photometry path 50B has both ends open, and its both ends are closed by a transparent cover 55. The discharge path 50C discharges an eluent of the photometry path 50B, and is connected to the waste fluid bath 15 through piping 76 (see FIG. 1).

The light source 51 irradiates an eluent flowing through the photometry path 50B with light. This light source 51 is arranged facing an end face 50Ba of the photometry path 50B (transparent cover 55) so that the optic axis L may pass the center of the photometry path 50B. The source 51 may also be selected in its wavelength range capable of light outgoing according to a concentration calculating technique in the calculating section 61 (see FIG. 3) described below. However, usually, means capable of light outgoing in the wavelength range of 400 to 500 nm, for example, a halogen lamp is used. As a matter of fact, means other than a halogen lamp, for example, means including one or a plurality of LED elements can be also used as the light source 51.

The beam splitter 52 divides light passing through the photometry path 50B among light going out of the light source 51 and makes the light enter the light receiving system 53 for measurement and the light receiving system 54 for reference. The splitter is placed at an inclination angle of 45 degrees on the optic axis L. Well-known, various apparatuses such as a semi-transparent mirror can be used as the beam splitter 52.

The light receiving system 53 for measurement selectively receives light of a target wavelength among light passing through the beam splitter 52 and is placed on the optic axis L. The light receiving system 53 for measurement includes a wavelength selector 53A and the light receiving element 53B for receiving light passing through the wavelength selector 53A. The wavelength selector 53A selects a wavelength of light that should be permeated according to the concentration calculating technique in the calculating section 61 (see FIG. 3) described below. This wavelength selector 53A can adopt well-known spectrum means such as an interference filter, a sharp-cut filter or a grating. A photodiode can be used as the light receiving element 53B.

The light receiving system 54 for reference acquires data for suppressing the influence of the turbidity and scattering of an eluent from the analytical column 40 (see FIG. 1) and selectively receives light of a reference wavelength of 500 nm among light the optical path of which is altered by reflection in the beam splitter 52. This light receiving system 74 for measurement includes the interference filter 54A that selectively permeates light of 500 nm and the light receiving element 54B for receiving light permeating the interference filter 54A. A photodiode can be used as the light receiving element 54B.

Figure 3:
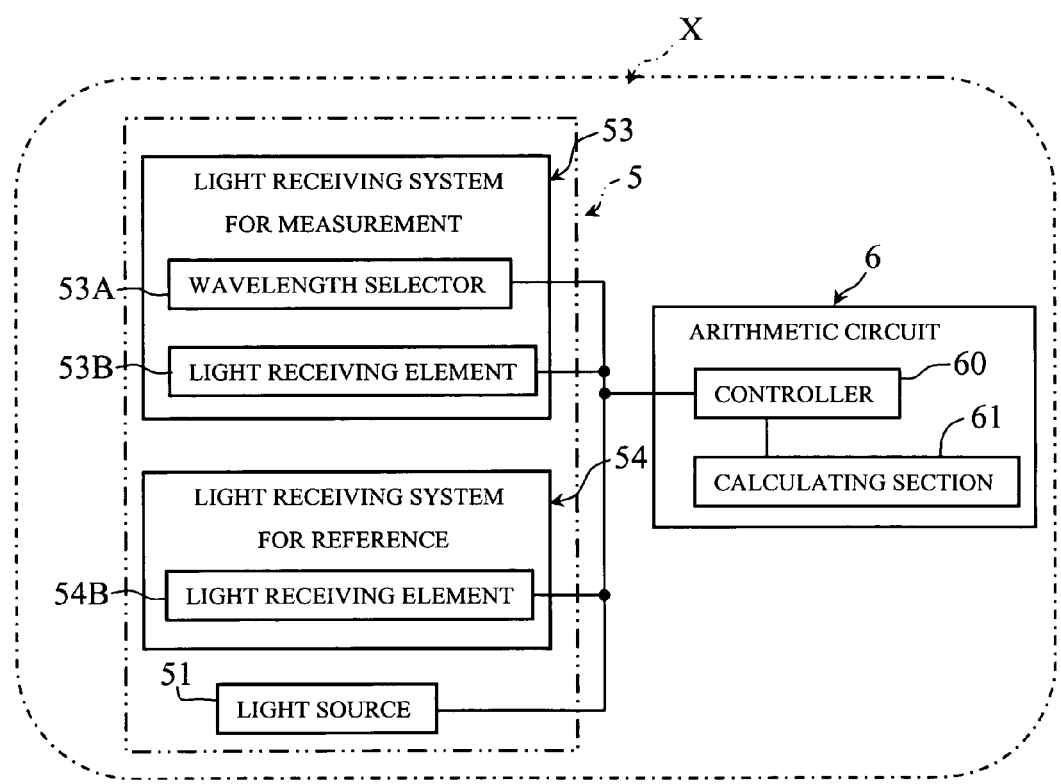
FIG. 3 is block diagram showing the main part of the HPLC apparatus shown in FIG. 1.

As shown in FIG. 3, the arithmetic circuit 6 includes a controller 60 and a calculating section 61.

The controller 60 controls the operation of each section. More specifically, the controller 60 controls the lighting and extinction of the light source 51, controls the wavelength selector 53A to select a wavelength of light received in the light receiving element 53B, or controls concentration arithmetic processing in the calculating section 61.

The calculating section 61 calculates the concentration of glycated hemoglobin in whole blood based on light reception results in the light receiving elements 53B, 54B. This calculating section 61 memorizes a program necessary for calculation and its operation is controlled by the controller 60.

Next, the operation of the HPLC apparatus X will be described with reference to the flow chart illustrated in FIG. 4 in addition to FIGS. 1 to 3.

In the HPLC apparatus X, when the instruction of measurement initiation is confirmed (S1), an eluent is supplied to the analytical column 40 (S2). The eluent is supplied from the eluent bottles 10, 11, 12 to the injection valve 43 by the power of the liquid feed pump 42 through the deaerator 2 and the manifold 41. Moreover, from which eluent bottles 10, 11, and 12 among a plurality of eluent bottles 10, 11, and 12 the eluent is supplied is selected by control of the manifold 41. An eluent supplied to the injection valve 43 is supplied to the analytical column 40 through piping 74.

The HPLC apparatus X further prepares a sample for introduction that should be introduced into the analytical column 40 (S3). Upon preparation of a sample for introduction, first, the blood sample 14 is collected from the blood collection tube 13.

The sampling nozzle 30 is operated to collect the blood sample 14 from the blood collection tube 13. The sampling nozzle 30 is operated to supply the blood sample 14 collected by the sampling nozzle 30 to the dilution bath 32. A hemolytic agent and a diluting fluid are further sequentially supplied to the dilution bath 32 from the preparation tank 31, and pipetting operation making use of the sampling nozzle 30 mixes the liquid within the dilution bath 32 to thereby prepare a sample for introduction.

The sample for introduction is introduced into the analytical column 40 (S4). For the introduction of a sample for introduction into the analytical column 40, the sample for introduction of the injection loop 44 is introduced into the analytical column 40 with an eluent by switch operation of the injection valve 43. In the analytical column 40, the introduction of the sample for introduction leads to adsorption of the glycated hemoglobin onto the filler. After adsorption of the glycated hemoglobin on the filler, the kind of eluent supplied to the analytical column 40 is properly changed using the manifold 41 to elute the glycated hemoglobin adsorbed on the filler.

On the other hand, when a fixed time passes from the introduction initiation of the sample for introduction, the injection valve 43 is switched to thereby continuously supply an eluent to the analytical column 40 and also wash the injection loop 44 (S5). On the other hand, at the same time as washing of the injection loop 44, as described previously, a sample for introduction is prepared using the blood sample 14 of the blood collection tube 13 different from the previous one (S3). After washing of the injection loop 44, a sample for introduction is introduced into the injection loop 44 again (S4). Such preparation (S3), introduction (S4) and washing (S5) of a sample for introduction are repeated depending on the number of blood collection tubes 13 (blood samples 14) to be measurement targets while the injection valves 43 are switched properly.

An eluent including glycated hemoglobin discharged from the analytical column 40 is supplied to the photometry cell 50 of the photometry mechanism 5 through piping 76 and then subjected to photometry (S6). An eluent is introduced into the photometry cell 50 through piping 75 and the introduction path 50A. This eluent passes through the photometry path 50B and the discharge path 50C and then is led into the waste fluid bath 15 through piping 76.

In the photometry mechanism 5, when an eluent from the analytical column 40 is passing through the photometry path 50B, the eluent is continuously irradiated with light by the light source 51. On the other hand, the light that passes through the photometry path 50B is divided in the beam splitter 52 and then receives light in the light receiving system 53 for measurement and the light receiving system 54 for reference. In the light receiving system 53 for measurement, light of a specific wavelength that passes through the wavelength selector 53A is selectively received in the light receiving element 53B. On the other hand, in the light receiving system 54 for reference, light of 500 nm that is a reference wavelength, passing through the interference filter 54A, is selectively received in the light receiving element 54B.

The light reception results in the light receiving elements 53B, 54B are output to the arithmetic circuit 6, and the concentration of the glycated hemoglobin is calculated in this arithmetic circuit 6 (S7).

Figure 5:
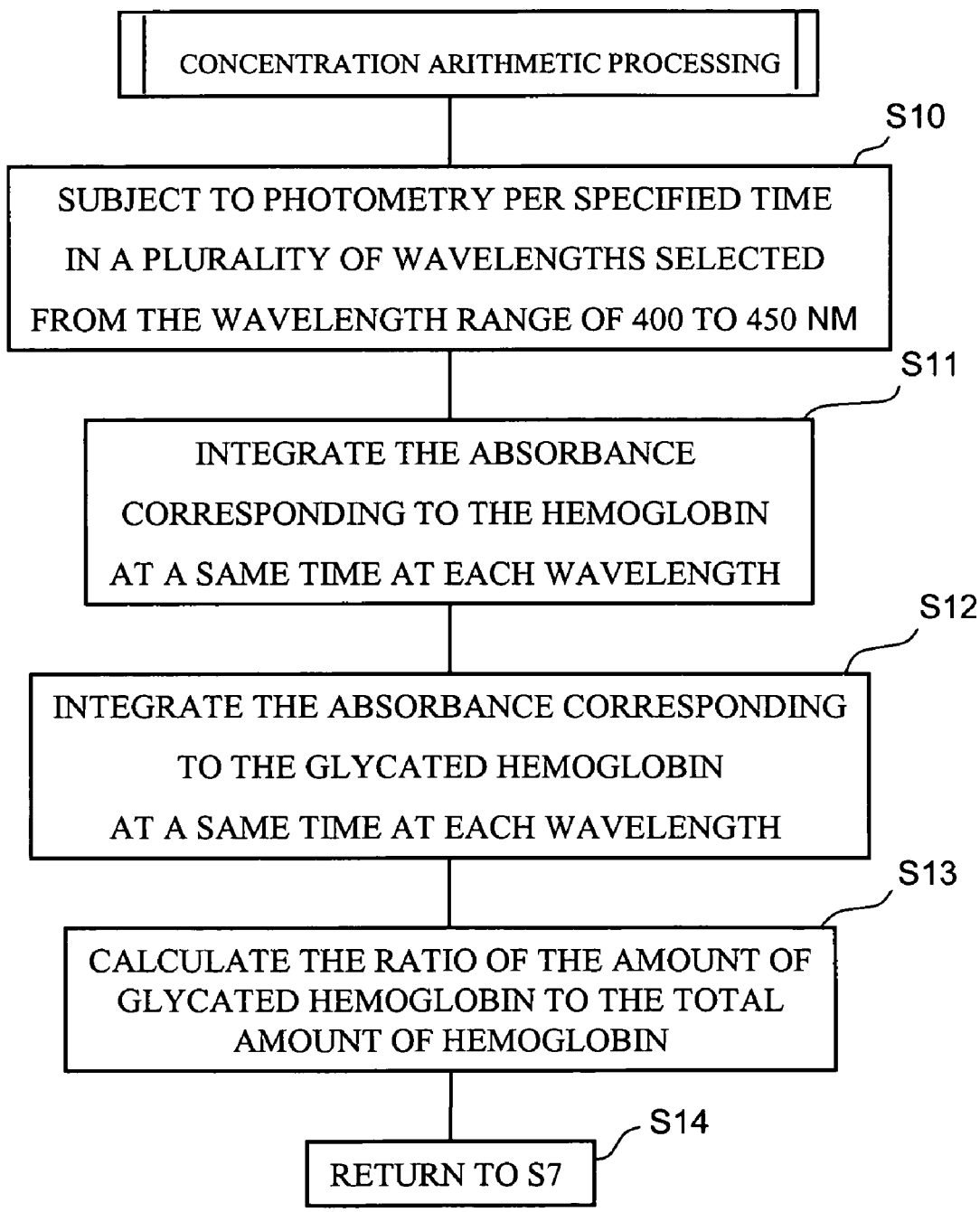
FIG. 5 is a flow chart for describing concentration measurement processing in an arithmetic circuit in the HPLC apparatus shown in FIG. 1.

Concentration arithmetic processing in the arithmetic circuit 6 is executed according to the procedure of the flow chart shown in FIG. 5.

First, by use of a plurality of wavelengths selected from the wavelength range of 400 to 450 nm, preferably 415 to 430 nm, the photometry is carried out per wavelength per specific time (S10). More specifically, light is continuously ejected from the light source 51, while the controller 60 controls the wavelength selector 53A and the wavelength of light received in the light receiving element 53B is made changed over time in the above wavelength range. That is, the wavelength of the light received in the light receiving element 53B is made continuously or intermittently changed. In addition, the photometry in which the wavelength is changed in the above wavelength range is repeated.

Figure 6:
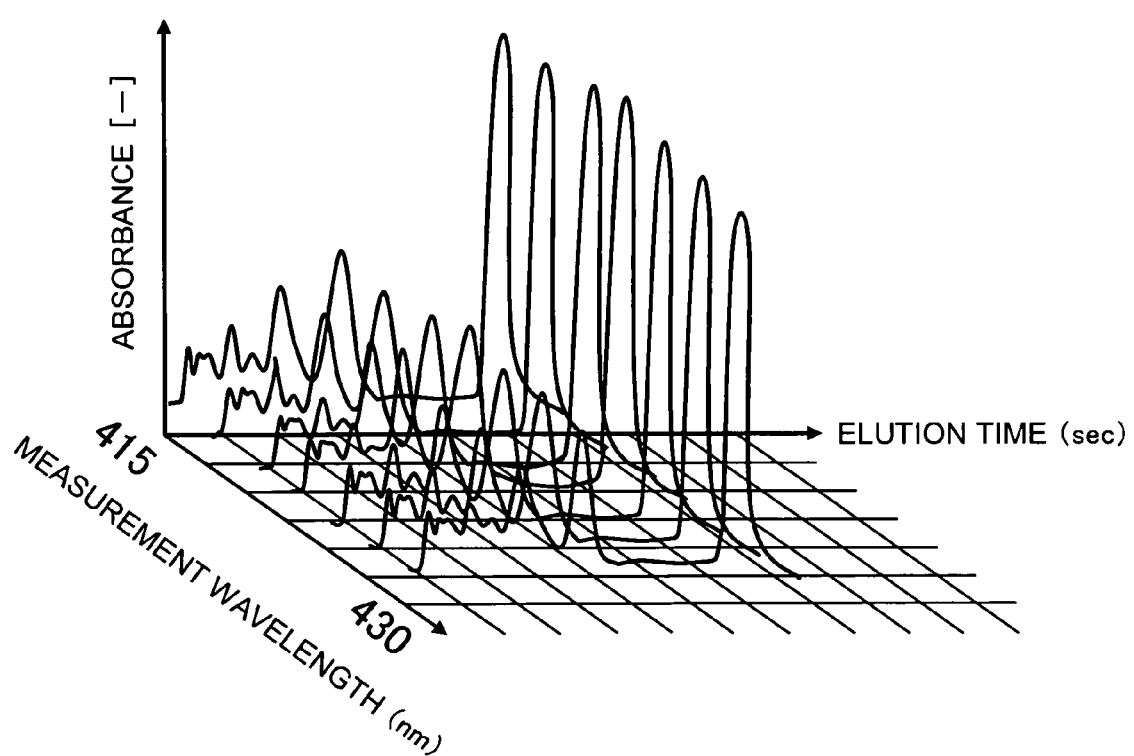
FIG. 6 is one example of a three dimensional chromatogram obtained in an arithmetic circuit.

Although FIG. 6 shows an example when the wavelength is intermittently changed, when the above time range is isochronally handled, a two-dimensional chromatogram is obtained for each measurement wavelength. If the measurement wavelength is made a variable, a three dimensional chromatogram in which the elution time, the absorbance and the measurement wavelength are made variables is obtained. In addition, though the interval of the measurement wavelength is set relatively large in FIG. 6, the interval of the measurement wavelength is actually extremely small (e.g., 0.1 to 2 nm). The plot points when the wavelength is made variable are not discrete, but more continuous.

Next, the absorbance corresponding to the hemoglobin at a same time at each wavelength is integrated (S11). In other words, the volume of the part corresponding to the hemoglobin in the three dimensional chromatogram in FIG. 6 is calculated as an integrated value of area of the part corresponding to the hemoglobin in the two dimensional chromatogram at each wavelength.

Next, the absorbance corresponding to the glycated hemoglobin at a same time at each wavelength is integrated (S12). In other words, the volume of the part corresponding to the glycated hemoglobin in the three dimensional chromatogram in FIG. 6 is calculated as an integrated value of area of the part corresponding to the hemoglobin in the two dimensional chromatogram at each wavelength.

Next, the proportion of the amount of glycated hemoglobin in the total amount of hemoglobin is calculated (S13). In other words, the proportion of the volume (integrated value) corresponding to the glycated hemoglobin among the volume (integrated value) corresponding to the three dimensional total amount of hemoglobin in FIG. 6 is calculated and taken as the concentration (%) of the glycated hemoglobin.

Figure 4:
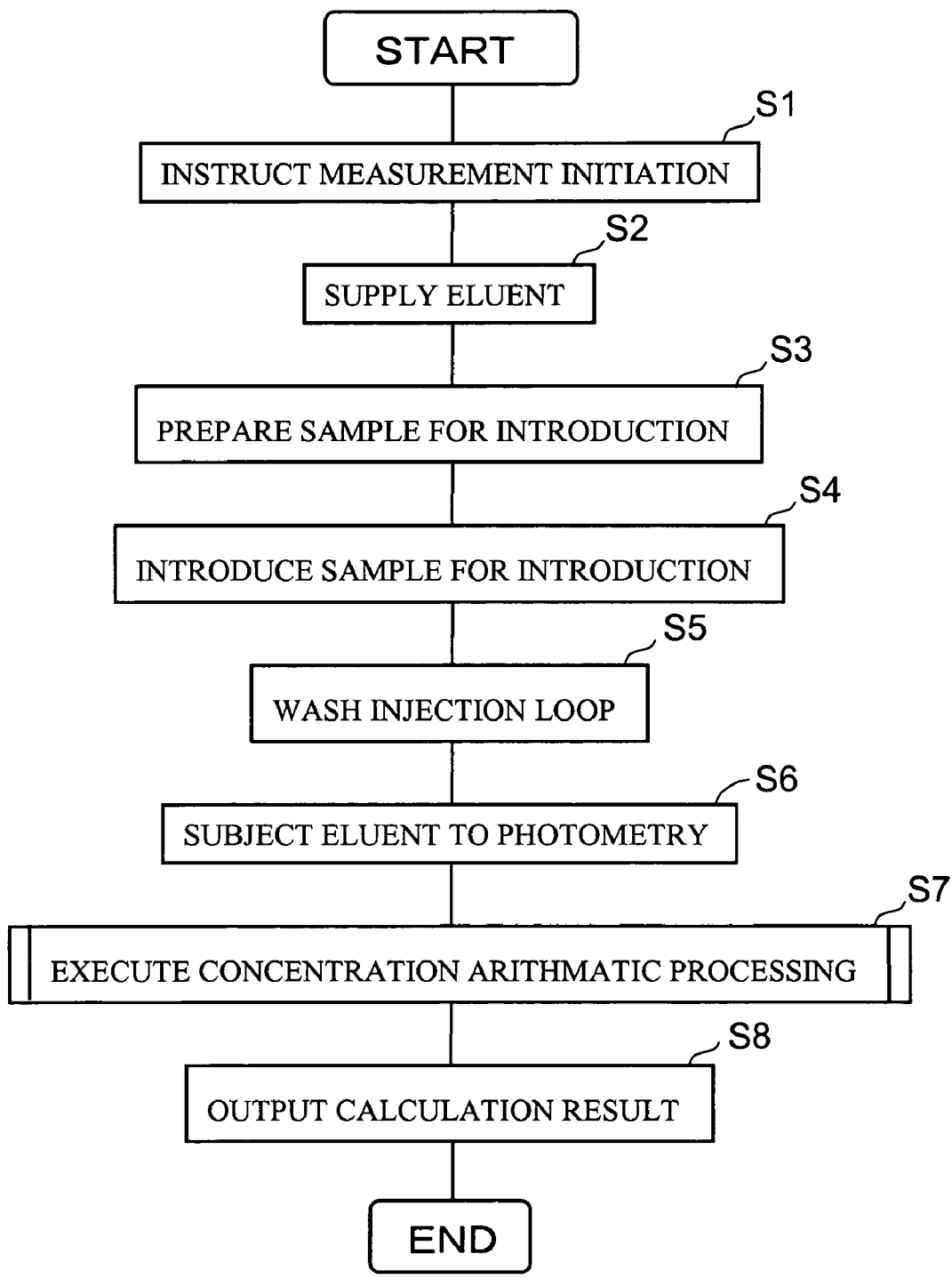
FIG. 4 is a flow chart for describing the operation of the HPLC apparatus shown in FIG. 1.

When the calculation in S13 is completed, the operation is returned to S7 in FIG. 4 (S14). That is, the calculation result in the arithmetic circuit 6 is displayed in a display panel (not illustrated) and printed out automatically or by a user's button operation (S8).

In this embodiment, the concentration of glycated hemoglobin is calculated in a wavelength range including 415 nm that is the maximum absorption wavelength of oxyhemoglobin and 430 nm that is the maximum absorption wavelength of deoxyhemoglobin based on absorption changes when the wavelength is continuously or intermittently changed. That is, the present invention does not calculate the concentration of glycated hemoglobin by mainly focusing on oxyhemoglobin, but calculates the concentration of glycated hemoglobin also in consideration of the influence of deoxyhemoglobin. Because of this, even when the ratio of the amounts of oxyhemoglobin and deoxyhemoglobin in hemoglobin varies due to the variation of the state of dissolved gas in a eluent or when the ratio of the amounts of oxyhemoglobin and deoxyhemoglobin in a sample for introduction to be introduced into the analytical column 40 varies, the calculation does not receive its influence. As a result, in this embodiment, when the concentration of glycated hemoglobin is measured in an environment in which the temperature outside the HPLC apparatus X (environmental temperature) varies or in states in which the environmental temperatures are different, or even when the variation of the oxygen concentration in a sample to be introduced into an analytical column is caused, the glycated hemoglobin concentration can be stably determined regardless of the ratio of the amounts of oxyhemoglobin and deoxyhemoglobin in an eluent.

Additionally, in the calculation of the concentration of glycated hemoglobin, for example, the proportions occupied by glycated hemoglobin in the total amount of hemoglobin are calculated based on a two dimensional chromatography at each measurement wavelength and also the mean value of the proportions of the glycated hemoglobin at each measurement wavelength is calculated and its mean value may be taken as the glycated hemoglobin concentration.

Next, a second embodiment of the present invention will be described with reference to FIGS. 3, 7 and 8.

Figure 7:
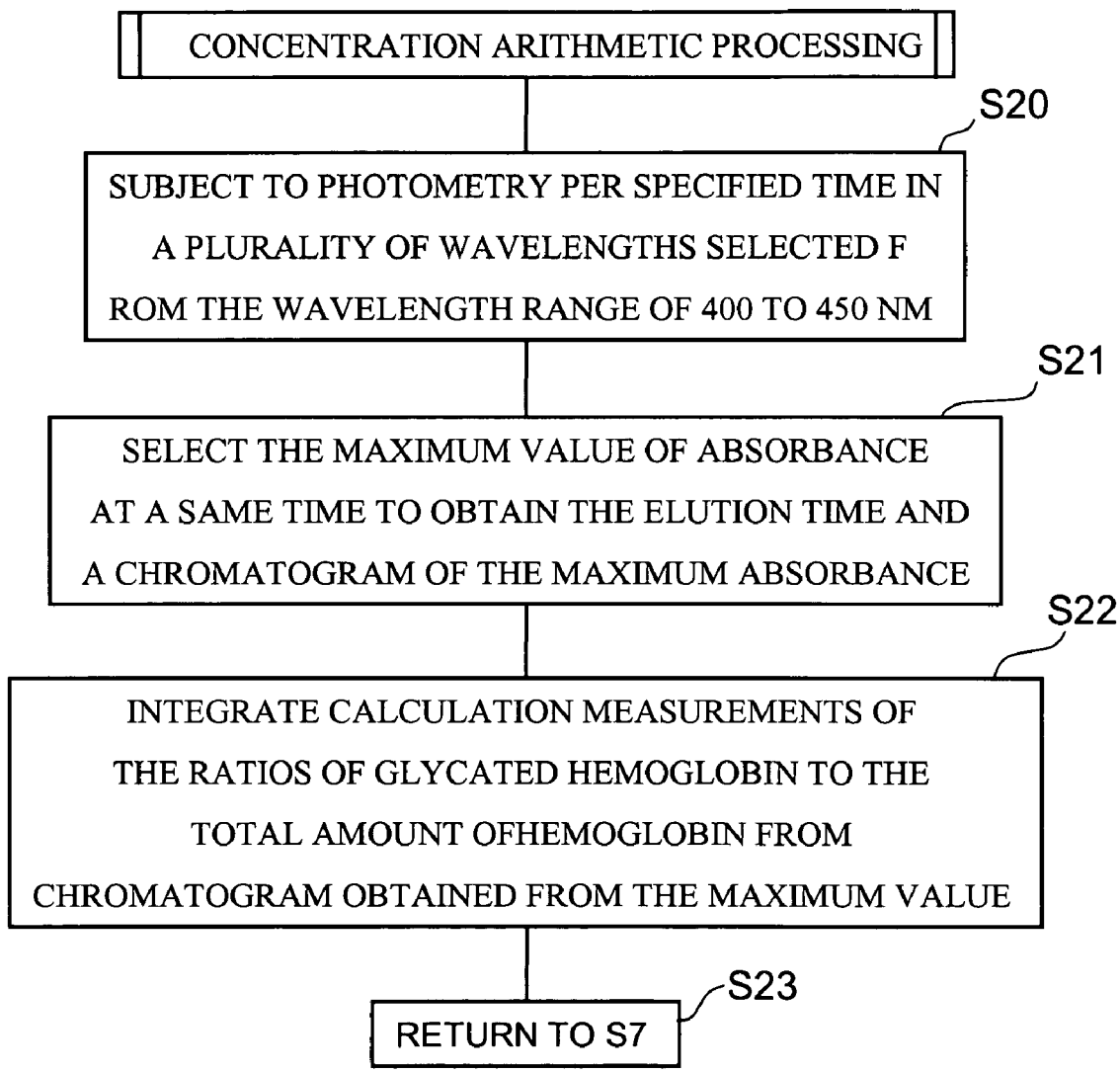
FIG. 7 is a flow chart for describing concentration measurement processing in an arithmetic circuit according to a second embodiment of the present invention.

In this embodiment, as illustrated in FIG. 7, the technique of concentration arithmetic processing in the arithmetic circuit 6 differs from the previous embodiment.

Figure 8A:
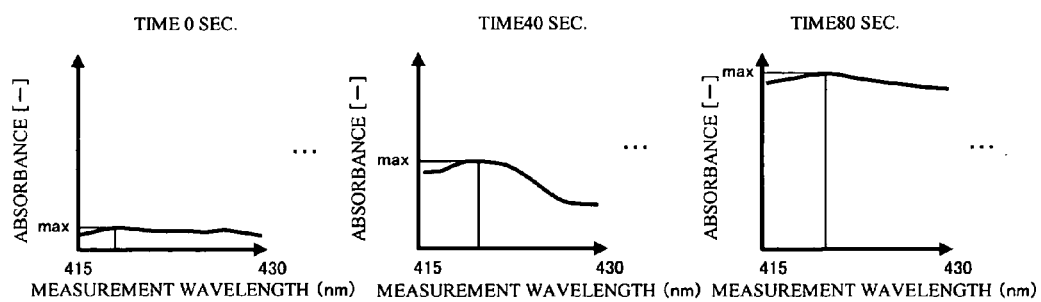
FIG. 8A is a graph indicating a relationship between the measurement wavelength and the absorbance at a specified time.

First, in a plurality of wavelengths selected from the wavelength range of 400 to 450 nm, preferably 415 to 430 nm, the photometry is carried out per specific time (S20). This point is similar to S10 (see FIG. 5) in the first embodiment. When the measurement wavelength is changed continuously or intermittently, a graph indicating the relationship between the measurement wavelength and the absorbance at each time is obtained as shown in FIG. 8A.

Figure 8B:
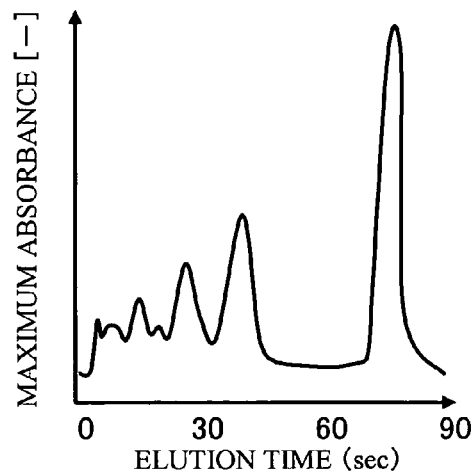
FIG. 8B is a two-dimensional chromatogram made based on maximum absorbance at a specified time.

Next, the maximum absorbance (max) at a same time is selected and a two dimensional chromatogram indicating the relationship between the elution time and the maximum absorbance is obtained as shown in FIG. 8B (S21).

Next, from the two dimensional chromatogram shown in FIG. 8B, the glycated hemoglobin concentration (%) is calculated as an area corresponding to the amount of glycated hemoglobin relative to the area corresponding to the total amount of hemoglobin (S22).

When processing in S22 is completed, the operation is returned to S7 in FIG. 4, the calculation result in the arithmetic circuit 6 is output to a display panel (not illustrated) or the like (S8).

This embodiment makes use of a wavelength range including 415 nm that is the maximum absorption wavelength of oxyhemoglobin and 430 nm that is the maximum absorption wavelength of deoxyhemoglobin, as measurement wavelengths and also of the maximum absorbance measured in their wavelength range to calculate the concentration of the glycated hemoglobin. Because of this, as in the case of the first embodiment of the present invention, the concentration of the glycated hemoglobin can be stably determined regardless of the ratio of the amounts of oxyhemoglobin and deoxyhemoglobin in an eluent from the analytical column 40.

Next, a third embodiment of the present invention will be described with reference to FIGS. 3, 9 and 10.

Figure 9:
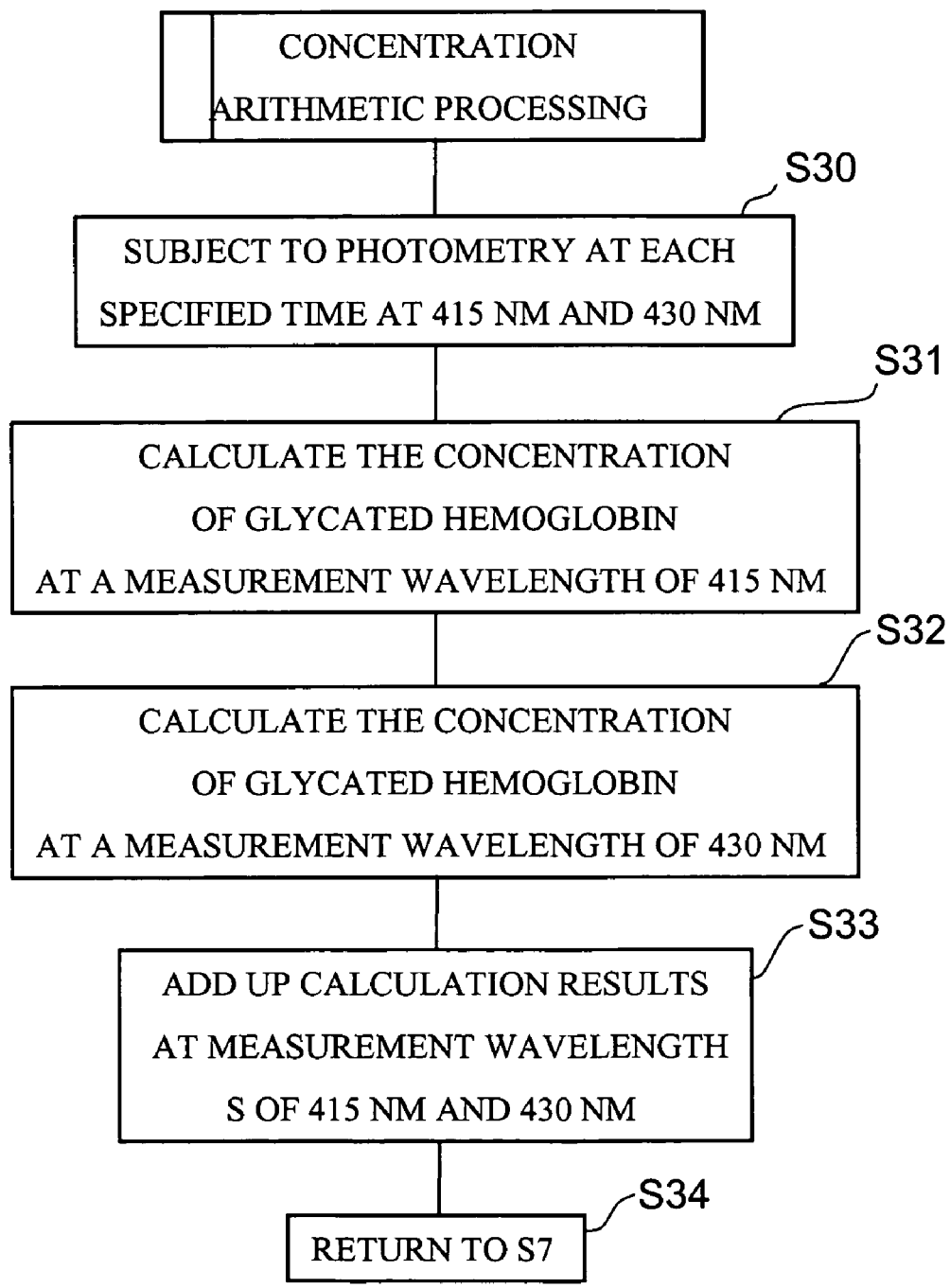
FIG. 9 is a flow chart for describing concentration measurement processing in an arithmetic circuit according to a third embodiment of the present invention.
Figure 10:
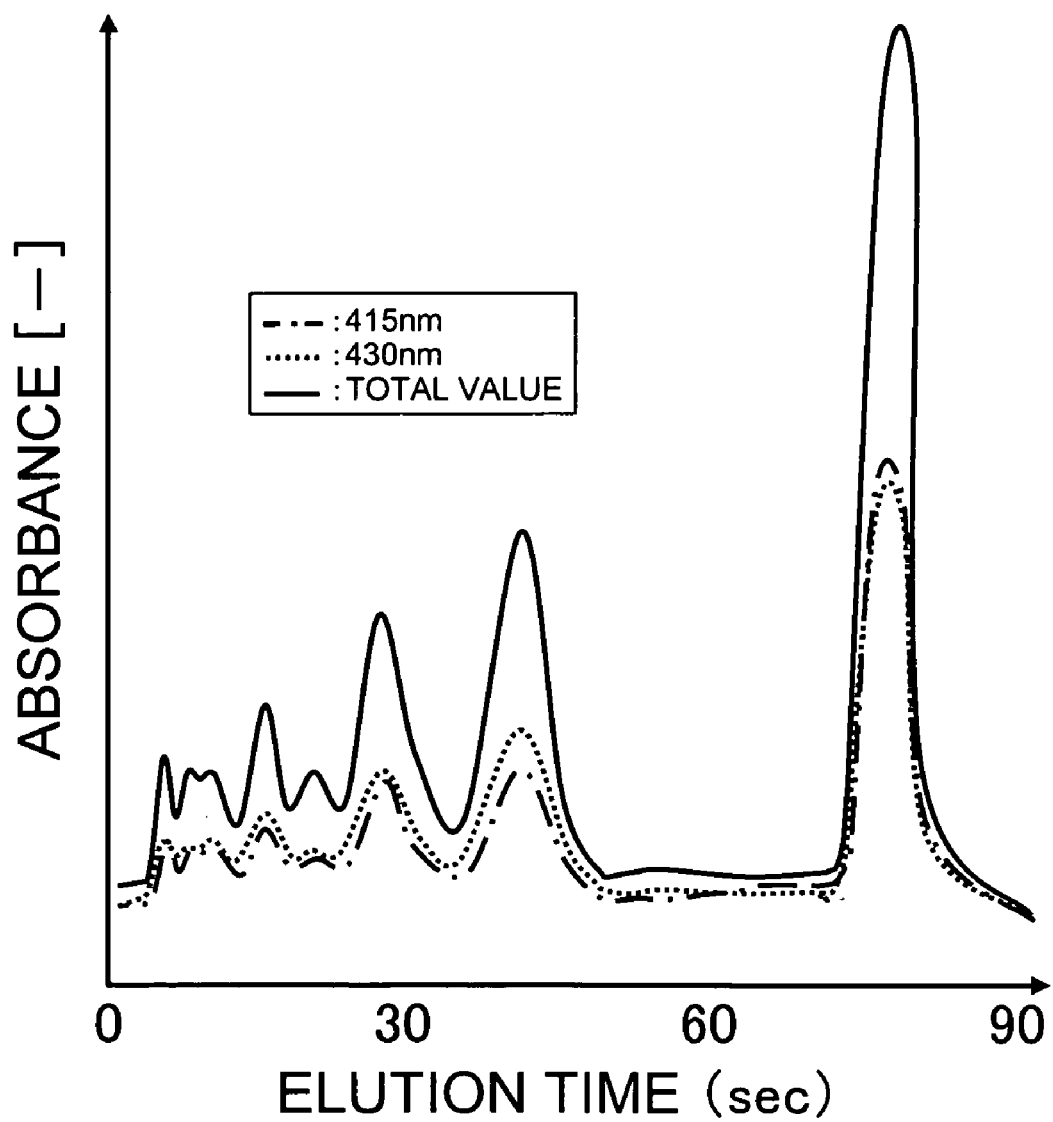
FIG. 10 shows two-dimensional chromatograms in a case of the absorbance of a measurement wavelength of 415 nm (dashed line), in a case of the absorbance of a measurement wavelength of 430 nm (chain line) and in a case of addition of the absorbances of the measurement wavelengths of 415 nm and 430 nm (solid line).

In this embodiment, as illustrated in FIG. 9, the technique of concentration arithmetic processing in the arithmetic circuit 6 differs from the previous embodiment.

First, photometry is carried out at 415 nm and 430 nm at each specified time (S30). More specifically, light is continuously ejected from the light source 51, while the controller 60 controls the wavelength selector 53A and the wavelength of light received in the light receiving element 53B is switched alternately between 415 nm and 430 nm. Such a measurement wavelength is repeatedly switched. As a result, as shown in FIG. 10, a two dimensional chromatogram of an oxyhemoglobin standard when the measurement wavelength is set at 415 nm (alternate long and short dash line of FIG. 10) and a two dimensional chromatogram of an deoxyhemoglobin standard when the measurement wavelength is set at 430 nm (chain line of FIG. 10) are obtained as the relationship between the elution time and the absorbance.

Next, the concentration of the glycated hemoglobin is calculated from the two dimensional chromatogram of the oxyhemoglobin standard when the measurement wavelength is set at 415 nm (alternate long and short dash line of FIG. 10) (S31).

Then, the concentration of the glycated hemoglobin is calculated from the two dimensional chromatogram of the deoxyhemoglobin standard when the measurement wavelength is set at 430 nm (chain line of FIG. 10) (S32).

Next, the concentration calculation result when the measurement wavelength is set at 415 nm and the concentration calculation result when the measurement wavelength is set at 430 nm are added up and taken as the concentration of the glycated hemoglobin (S33).

When processing in S33 is completed, the operation is returned to S7 in FIG. 4 (S34), the calculation result in the arithmetic circuit 6 is output to a display panel (not illustrated) or the like (S8).

This embodiment calculates the glycated hemoglobin concentration by adding up, as measurement wavelengths, a measurement result of 415 nm that is the maximum absorption wavelength of oxyhemoglobin and a measurement result of 430 nm that is the maximum absorption wavelength of deoxyhemoglobin. Because of this, as in the case of the first embodiment of the present invention, the concentration of the glycated hemoglobin can be stably determined regardless of the ratio of the amounts of oxyhemoglobin and deoxyhemoglobin in an eluent from the analytical column 40.

In this embodiment, the concentration of the glycated hemoglobin may also be calculated based on a chromatogram (solid line of FIG. 10) obtained by adding up a chromatogram when the measurement wavelength is set at 415 nm and a chromatogram when the measurement wavelength is set at 430 nm.

Additionally, the measurement wavelength when the chromatogram of the oxyhemoglobin standard is obtained is not limited to 415 nm, but may be selected from the wavelength range of 400 to 420 nm; the measurement wavelength when the chromatogram of the deoxyhemoglobin standard is obtained is not limited to 430 nm, but may be selected from the wavelength range of 420 to 440 nm.

The present invention is not limited to the embodiment previously described, and can be changed to various embodiments. For example, in the concentration arithmetic processing previously described, although the amount of hemoglobin is acquired as absorbance, it is not necessarily as absorbance. The amount of hemoglobin may be acquired as transmissivity or simply as the amount of light received.

Moreover, the method of distinguishing and recognizing light of a plurality of measurement wavelengths in the photometry mechanism 5 may be, in addition to a method of doing it with one of the light receiving elements 53B, a method of disposing light receiving elements according to the number of measurement wavelengths or using a light-emitting element having a light receiving area.

The method of selecting the wavelength of light (measurement wavelength) received by the light receiving element 53B of the light receiving system 53 for measurement in the photometry mechanism 5 adopts a configuration of disposing the wavelength selector 53A in light receiving system 53 for measurement and can adopt a configuration of placing a wavelength selector between the light source 1 and the photometry cell 50.

The present invention is not limited to an HPLC apparatus for measuring the concentration of glycated hemoglobin in blood and can also be further applied to a case of using a specimen other than blood or to a liquid chromatography apparatus other than an HPLC apparatus or to other apparatus of measuring the concentration of glycated hemoglobin.

EXAMPLE

Example 1

In this example, when the measurement wavelength was changed and the concentration of glycated hemoglobin was measured, the effect of the environmental temperature on measurements was studied.

The concentration of glycated hemoglobin was determined at environmental temperatures of 10° C., 20° C., and 30° C. by adopting as a light receiving element a photodiode array ("UV-visible multi-wavelength detector MD-910"; manufactured by Jasco Co.) using a glycated hemoglobin measuring apparatus ("ADAMS A1c HA-8160"; manufactured by Arkray, Inc.). For the concentration of glycated hemoglobin, the total amount of hemoglobin and the amount of glycated hemoglobin were each measured per 1 nm in the wavelength range of 415 to 430 nm. Then, the concentration of the glycated hemoglobin was calculated as the proportion occupied by the integrated value of the glycated hemoglobin relative to the integrated value of the total amount of hemoglobin in the previous wavelength range.

The blood (diabetic patient blood) collected from a healthy individual and the blood collected from a diabetic patient (diabetic patient blood) were used as specimens. The measurement results of the glycated hemoglobin are shown Table 1 and FIG. 11 below.

TABLE 1

|  | Glycated hemoglobin measurements | | |
| --- | --- | --- | --- |
|  | 10° C. | 20° C. | 30° C. |
| Healthy individual specimen | 4.41% | 4.47% | 4.40% |
| Diabetic patient specimen | 8.40% | 8.43% | 8.33% |

Comparative Example 1

In this Comparative Example, when the measurement wavelength was fixed at 415 nm that is the maximum absorption wavelength of the oxyhemoglobin and the concentration of glycated hemoglobin was measured, the effect of the environmental temperature on measurements was studied.

The concentrations of the glycated hemoglobin were basically measured in the same conditions as in Example 1 with the exception that the measurement wavelength was fixed. The concentration was calculated as the proportion occupied by the amount of the glycated hemoglobin in the total amount of glycated hemoglobin. The measurement results of the glycated hemoglobin are shown Table 2 and FIG. 12 below.

TABLE 2

|  | Glycated hemoglobin measurements | | |
| --- | --- | --- | --- |
|  | 10° C. | 20° C. | 30° C. |
| Healthy individual specimen | 4.33% | 4.73% | 5.10% |
| Diabetic patient specimen | 8.41% | 8.83% | 9.68% |

Figure 12:
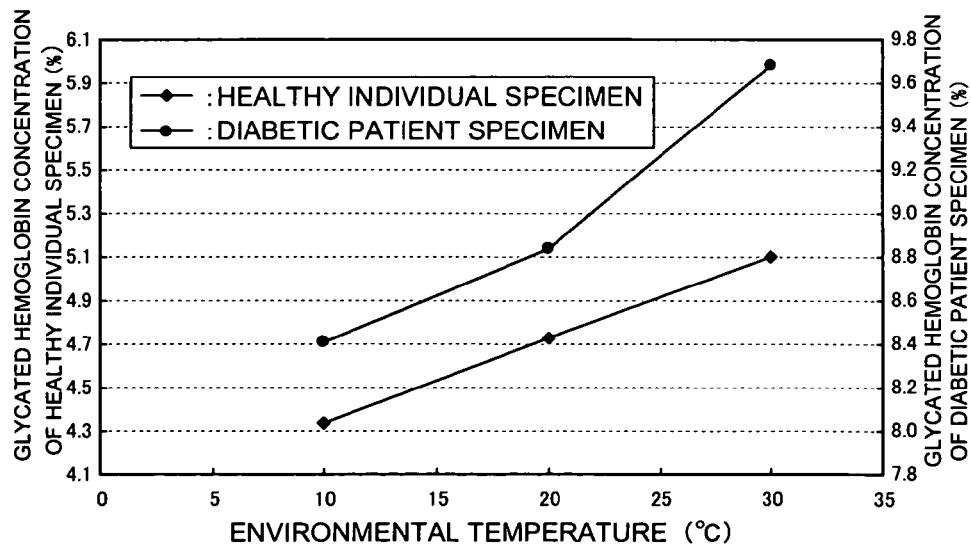
FIG. 12 is a graph indicating a relationship between the environmental temperature and the concentration of glycated hemoglobin in Comparative Example 1.
Figure 13:
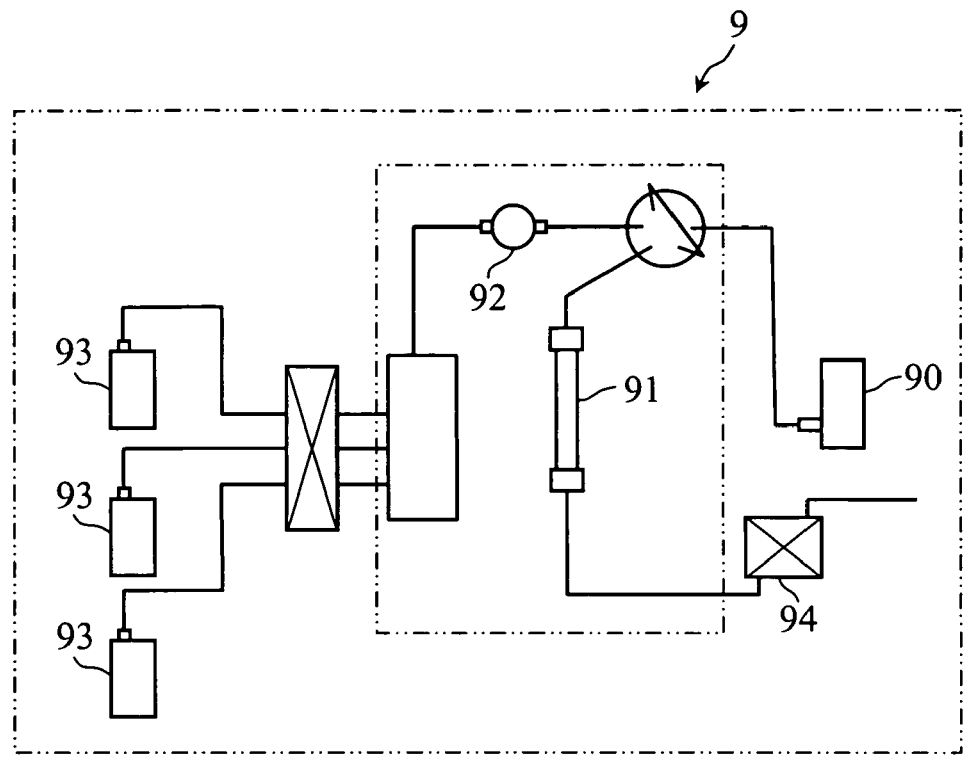
FIG. 13 is a schematic block diagram showing an HPLC apparatus that is one example of a conventional glycated hemoglobin measuring apparatus.
Figure 14:
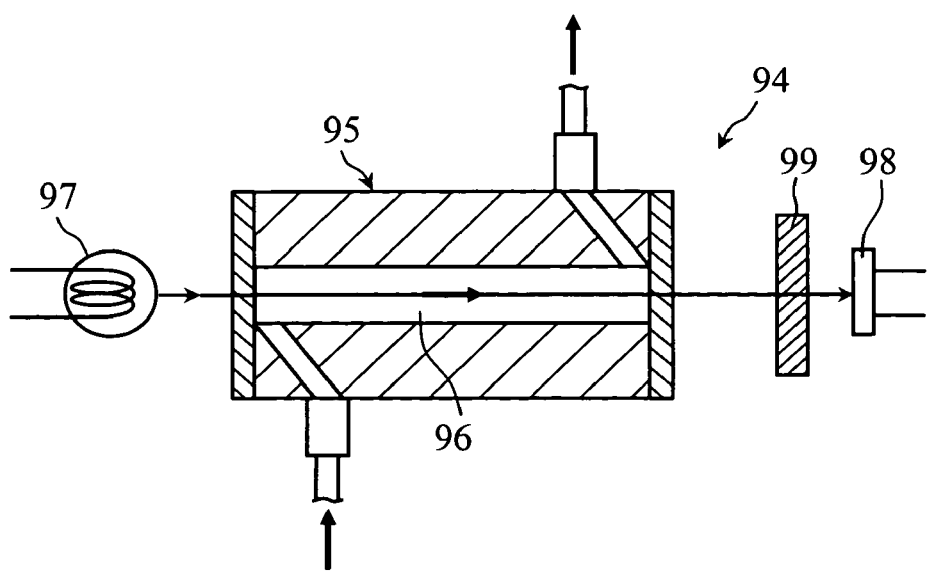
FIG. 14 is a cross-sectional view for describing a photometry mechanism in the HPLC apparatus shown in FIG. 13.
Figure 15:
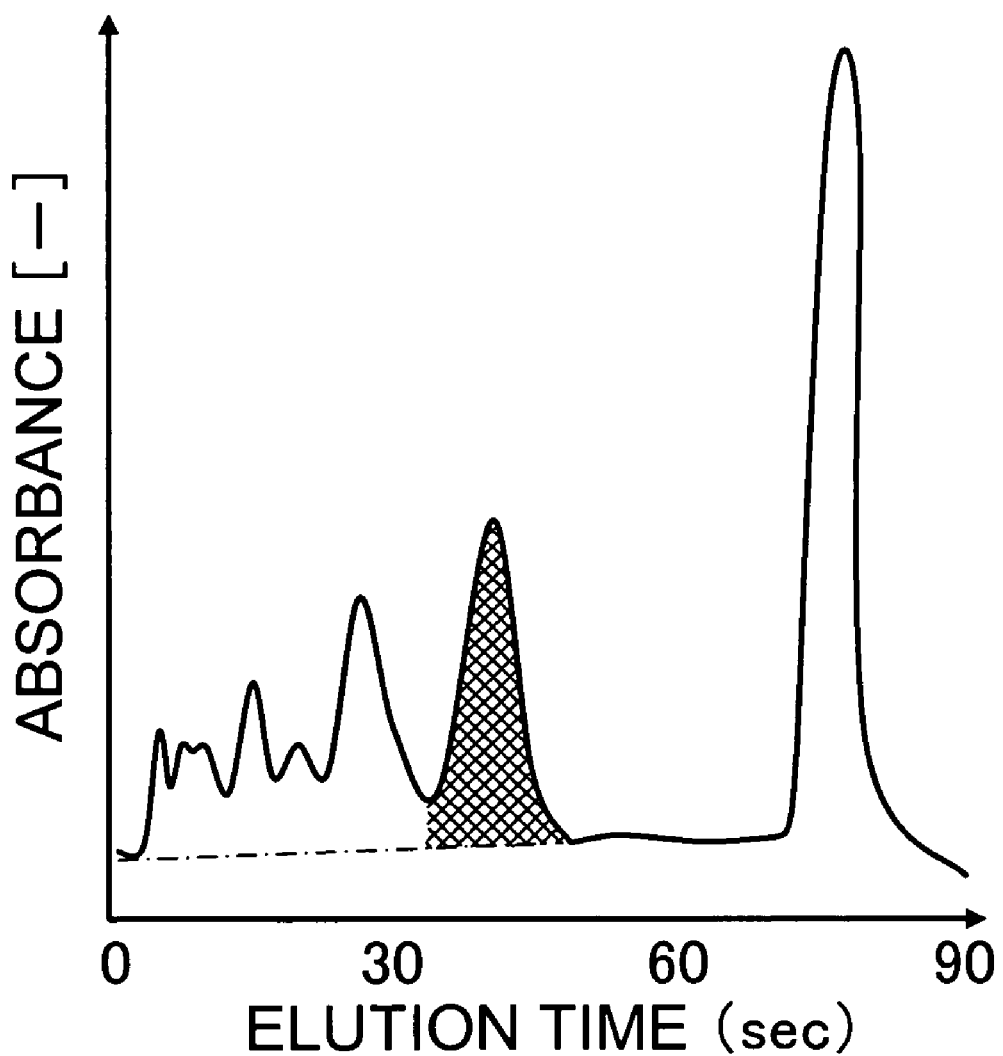
FIG. 15 is one example of a chromatogram obtained in the HPLC apparatus shown in FIG. 13.

When, as in Comparative Example 1, the measurement wavelength was fixed at 415 nm that is the maximum absorption wavelength of the oxyhemoglobin and the glycated hemoglobin was measured, Table 2 and FIG. 12 show that as the environmental temperature becomes high, the measurements were increased, and the measurements were greatly affected by the environmental temperature.

Figure 11:
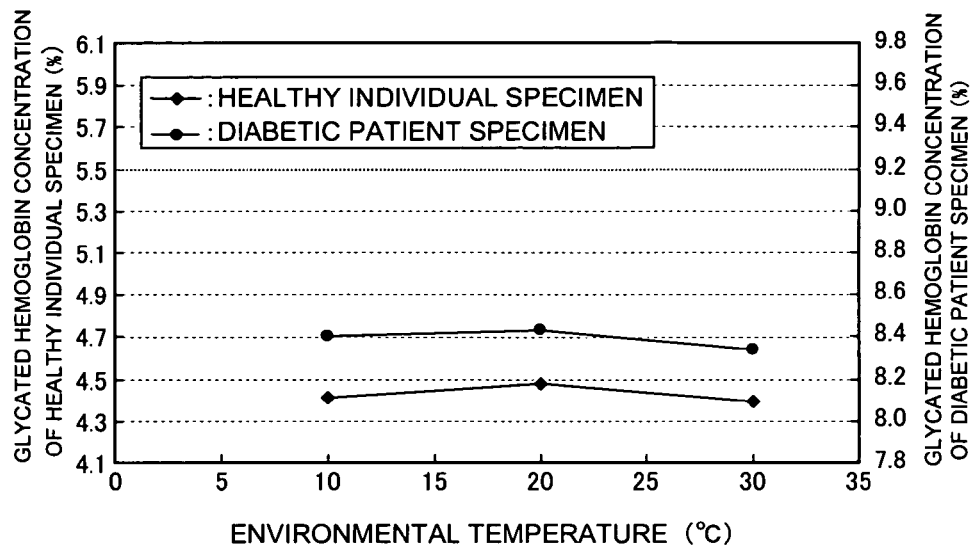
FIG. 11 is a graph indicating a relationship between the environmental temperature and the concentration of glycated hemoglobin in Example 1.

On the other hand, as in Example 1, in the case where the glycated hemoglobin concentrations were calculated by integrated values when the measurement wavelength was changed between the maximum absorption wavelength (415 nm) of the oxyhemoglobin and the maximum absorption wavelength (430 nm) of the deoxyhemoglobin, Table 1 and FIG. 11 show that the measurements were not so affected by the environmental temperature and substantially became a constant value, even if the environmental temperature was changed between 10 and 30° C.

This shows that in the case where the glycated hemoglobin concentrations were calculated by integrated values when the measurement wavelength was changed between the maximum absorption wavelength (415 nm) of the oxyhemoglobin and the maximum absorption wavelength (430 nm) of the deoxyhemoglobin, the concentration of glycated hemoglobin is not affected by the environmental temperature (dissolved oxygen concentration of an eluent) and the dissolved oxygen concentration, and a precise and stable measurement of the glycated hemoglobin concentration is possible.

The invention claimed is:

1. A method of measuring a concentration of glycated hemoglobin in a sample, the method comprising:
eluting the sample;
irradiating the sample with light; and
measuring the concentration of glycated hemoglobin in the sample based on plurality of lights of measurement wavelength each having a peak wavelength in the wavelength range of 400 to 450 nm, the plurality of lights of measurement wavelength passing through and traveling from the sample to a light receiving section as a result of the sample being irradiated, wherein the concentration of the glycated hemoglobin is calculated based on a three dimensional chromatogram in which the measurement wavelength, an elution time of the sample, and an amount of light received in the light receiving section are made variables.

2. The method of measuring the concentration of glycated hemoglobin according to claim 1, wherein
the sample is produced by hemolyzing a blood cell.

3. The method of measuring the concentration of glycated hemoglobin according to claim 1, wherein the amount of light received by the light receiving section corresponds to an absorbance of light by the sample.

4. A method of measuring a concentration of glycated hemoglobin in a sample, the method comprising:
irradiating the sample with light; and
measuring the concentration of glycated hemoglobin in the sample based on a first quantity of light that is an amount of light that has a peak wavelength in the wavelength range of 400 to 420 nm and passes through and travels from the sample as a result of the sample being irradiated, and a second quantity of light that is an amount of light that has a peak wavelength in the wavelength range of 420 to 440 nm and passes through and travels from the sample as a result of the sample being irradiated, wherein
the concentration of glycated hemoglobin is obtained by calculating the concentration of oxyhemoglobin or a value that correlates to the concentration of oxyhemoglobin based on the first quantity of light, and by calculating the concentration of deoxyhemoglobin or a value that correlates to the concentration of deoxyhemoglobin based on the second quantity of light, and
by adding up the oxyhemoglobin concentration or the value that correlates to the oxyhemoglobin concentration and the deoxyhemoglobin concentration or the value that correlates to the deoxyhemoglobin concentration.

5. A method of measuring a concentration of glycated hemoglobin in a sample, the method comprising:
eluting the sample;
irradiating the sample with light; and
measuring the concentration of glycated hemoglobin in the sample based on a first quantity of light that is an amount of light that has a peak wavelength in the wavelength range of 400 to 420 nm and passes through and travels from the sample to a light receiving section as a result of the sample being irradiated, and a second quantity of light that is an amount of light that has a peak wavelength in the wavelength range of 420 to 440 nm and passes through and travels from the sample to the light receiving section as a result of the sample being irradiated, wherein
the concentration of glycated hemoglobin is calculated based on a chromatogram produced by overlapping a first chromatogram that corresponds to oxyhemoglobin indicating the relationship between an elution time of the sample and an amount of light received in the light receiving section based on the first quantity of light and a second chromatogram that corresponds to deoxyhemoglobin indicating the relationship between the elution time of the sample and an amount of light received in the light receiving section based on the second quantity of light.

6. An apparatus for measuring a concentration of glycated hemoglobin in a sample, the apparatus comprising:
an eluting mechanism for eluting the sample;
a photometry mechanism including a light source and a light receiving section, wherein the photometry mechanism irradiates the sample with light from the light source, the light receiving section receives light that passes through and travels from the sample as a result of the sample being irradiated, and the photometry mechanism is configured to pass a plurality of lights of measurement wavelength each having a peak wavelength in the wavelength range of 400 to 450 nm through the sample and to receive light in the light receiving section after passing through and traveling from the sample; and a calculating section configured to calculate the glycated hemoglobin concentration in the sample based on a three dimensional chromatogram in which the measurement wavelength, an elution time of the sample, and an amount of light received by the light receiving section are made variables.

7. The apparatus for measuring the concentration of glycated hemoglobin according to claim 6, wherein
the sample is produced by hemolyzing a blood cell.

8. The apparatus for measuring the concentration of glycated hemoglobin according to claim 6, wherein the amount of light received by the light receiving section corresponds to an absorbance of light by the sample.

9. An apparatus for measuring a concentration of glycated hemoglobin in a sample, the apparatus comprising:

a photometry mechanism including a light source and a light receiving section, wherein the photometry mechanism irradiates the sample with light from the light source, the light receiving section receives light that passes through and travels from the sample as a result of the sample being irradiated, and the photometry mechanism is configured to pass a plurality of lights of measurement wavelength each having a peak wavelength in the wavelength range of 400 to 450 nm through the sample and to receive light in the light receiving section after passing through and traveling from the sample; and a calculating section configured to calculate the glycated hemoglobin concentration in the sample based on a first quantity of light that is an amount of light having a peak wavelength in the wavelength range of 400 to 420 nm, passing through and traveling from the sample, and a second quantity of light that is an amount of light having a peak wavelength in the wavelength range of 420 to 440 nm, passing through and traveling from the sample, wherein the calculating section is configured to calculate the concentration of oxyhemoglobin or a value that correlates to the concentration of oxyhemoglobin based on the first quantity of light on the one hand, and to calculate the concentration of deoxyhemoglobin or a value that correlates to the concentration of deoxyhemoglobin based on the second quantity of light on the other, and also to add up the oxyhemoglobin concentration or the value that correlates to the concentration of oxyhemoglobin and the deoxyhemoglobin concentration or the value that correlates to the concentration of deoxyhemoglobin to thereby calculate the concentration of glycated hemoglobin in the sample.

10. An apparatus for measuring a concentration of glycated hemoglobin in a sample, the apparatus comprising:

an eluting mechanism for eluting the sample;

a photometry mechanism including a light source and a light receiving section, wherein the photometry mechanism irradiates the sample with light from the light source, the light receiving section receives light that passes through and travels from the sample as a result of the sample being 2irradiated, and the photometry mechanism is configured to pass a plurality of lights of measurement wavelength each having a peak wavelength in the wavelength range of 400 to 450 nm through the sample and to receive light in the light receiving section after passing through and traveling from the sample; and a calculating section configured to calculate the glycated hemoglobin concentration in the sample based on a first quantity of light that is an amount of light having a peak wavelength in the wavelength range of 400 to 420 nm, passing through and traveling from the sample, and a second quantity of light that is an amount of light having a peak wavelength in the wavelength range of 420 to 440 nm, passing through and traveling from the sample, wherein the calculating section is further configured to calculate the concentration of glycated hemoglobin in the sample based on a chromatogram produced by overlapping a first chromatogram that corresponds to oxyhemoglobin indicating the relationship between an elution time of the sample and an amount of light received in the light receiving section based on the first quantity of light and a second chromatogram that corresponds to deoxyhemoglobin indicating the relationship between the elution time of the sample and an amount of light received in the light receiving section based on the second quantity of light.

* * * * *